United States Patent [19]
Sasaki et al.

[11] Patent Number: 5,690,624
[45] Date of Patent: Nov. 25, 1997

[54] DISPOSABLE DIAPER

[75] Inventors: Toru Sasaki; Makoto Suekane; Kenichi Hisada, all of Ehime-ken, Japan

[73] Assignee: Uni-Charm Corporation, Ehime-ken, Japan

[21] Appl. No.: 757,863

[22] Filed: Nov. 27, 1996

[30] Foreign Application Priority Data

Nov. 29, 1995 [JP] Japan ..................... 7-310874

[51] Int. Cl.$^6$ .............................. A61F 13/15; A61F 13/20
[52] U.S. Cl. ........................ 604/361; 604/380; 604/385.1
[58] Field of Search ....................... 604/358, 361, 604/364, 380, 385.1

[56] References Cited

U.S. PATENT DOCUMENTS

| | | |
|---|---|---|
| 3,675,654 | 7/1972 | Baker et al. . |
| 3,759,261 | 9/1973 | Wang ........................................ 604/361 |
| 4,192,311 | 3/1980 | Felfoldi . |
| 4,287,153 | 9/1981 | Townsend ................................ 604/361 |
| 4,507,121 | 3/1985 | Leung ...................................... 604/361 |
| 4,705,513 | 11/1987 | Sheldon et al. .......................... 604/361 |
| 4,810,562 | 3/1989 | Okawa et al. . |
| 5,354,289 | 10/1994 | Mitchell et al. ......................... 604/361 |

FOREIGN PATENT DOCUMENTS 3-58416  6/1991  Japan .

*Primary Examiner*—P. Zuttarelli
*Attorney, Agent, or Firm*—Lowe, Price, LeBlanc & Becker

[57] ABSTRACT

A disposable diaper is provided with an indicator adapted to be revealed as it is wetted with discharged urine and to tell a mother her baby's urination. The indicator comprises a hydrophilic base sheet, a first coating layer formed on one side of the base sheet so as to develop its proper color as the indicator is wetted with urine, and a second coating layer formed on the other side of the base sheet or upper surface of the first coating layer and intermittently bonded to the inner surface of the backsheet so that the second coating layer covers up the first coating layer. The second coating layer becomes transparent as the indicator is wetted with urine.

10 Claims, 3 Drawing Sheets

DISPOSABLE DIAPER

BACKGROUND OF THE INVENTION

The present invention relates to a disposable diaper and more particularly to a disposable diaper provided with an indicator serving to tell a mother her baby has urinated.

Japanese Laid-Open Utility Model Application No. Hei3-58416 discloses a disposable diaper employing indicator means having a color changing layer formed on an inner surface of a backsheet of the diaper and a colored permeable layer formed to cover the color changing layer. With the known indicator means, a quantity of urine discharged onto the diaper permeates through the permeable layer into the color changing layer which is thereupon made transparent and transmits the color of the permeable layer therethrough so that the mother may visually recognize this color externally of the diaper and be informed that the diaper should be exchanged with a fresh one.

The indicator means employed by the above-mentioned disposable diaper is certainly provided with a color revealing mechanism but the diaper includes no mechanism to assure permeation of urine into the indicator means. The indicator means comprising the color changing and permeable layers is formed on a hydrophobic polyethylene film of which the backsheet is made and therefore there is a problem that the indicator means as well as a region surrounding this means can not be easily wetted with urine. While it may be contemplated that bonding the indicator means to a liquid-absorbent core of the diaper with use of hydrophilic adhesive through which the desired permeation of urine into the indicator means may be achieved, there is found no adhesive able to meet such purpose, i.e., there is no adhesive which can be cured as rapidly that is compatible with a high rate of production of diapers. Accordingly, it is doubtful whether this indicator means will be reliably responsive to urination to be revealed or not. In addition, the backsheet made of polyethylene does not absorb various pigments used to form the color changing layer and the permeable layer, so the diaper manufacturing process can not proceed from one step to the subsequent step before much time is spent for adequately drying these layers. With a consequence, the productivity of the diapers is significantly limited.

SUMMARY OF THE INVENTION

In view of the problem as has been described above, it is a principal object of the invention to provide a disposable diaper so improved that the urine permeation into the indicator means can be facilitated without affecting the productivity of the diaper.

The object set forth above is achieved, according to the invention, by a disposable diaper comprising a liquid-permeable topsheet, a liquid-impermeable backsheet, a liquid-absorbent core disposed therebetween, and indicator means provided on a front or rear region of the diaper so as to be revealed as the indicator means is wetted with body fluids and thereby to allow occurrence of body fluid excretion to be recognized externally of the diaper, the disposable diaper being characterized by that:

a. the backsheet is light-transmissive;

b. the indicator means comprises a hydrophilic base sheet, a first coating layer formed on one side of the base sheet and having a color different from that of the base sheet, and a second coating layer formed on the other side of the base sheet or an upper surface of the first coating layer so as to substantially cover up the color of the first coating layer when the indicator means is dry but to be made transparent and thereby to reveal the color as the indicator means is wetted with urine;

c. the first coating layer comprises at least one of silica and alumina particles, and water-absorptive binder and colorant;

d. the second coating layer comprises at least one of silica and alumina particles, and hydrophilic binder; and e. the indicator means is attached to the diaper by intermittently bonding the second coating layer to an inner surface of the backsheet.

DESCRIPTION OF THE PREFERRED EMBODIMENTS

Figure 1:
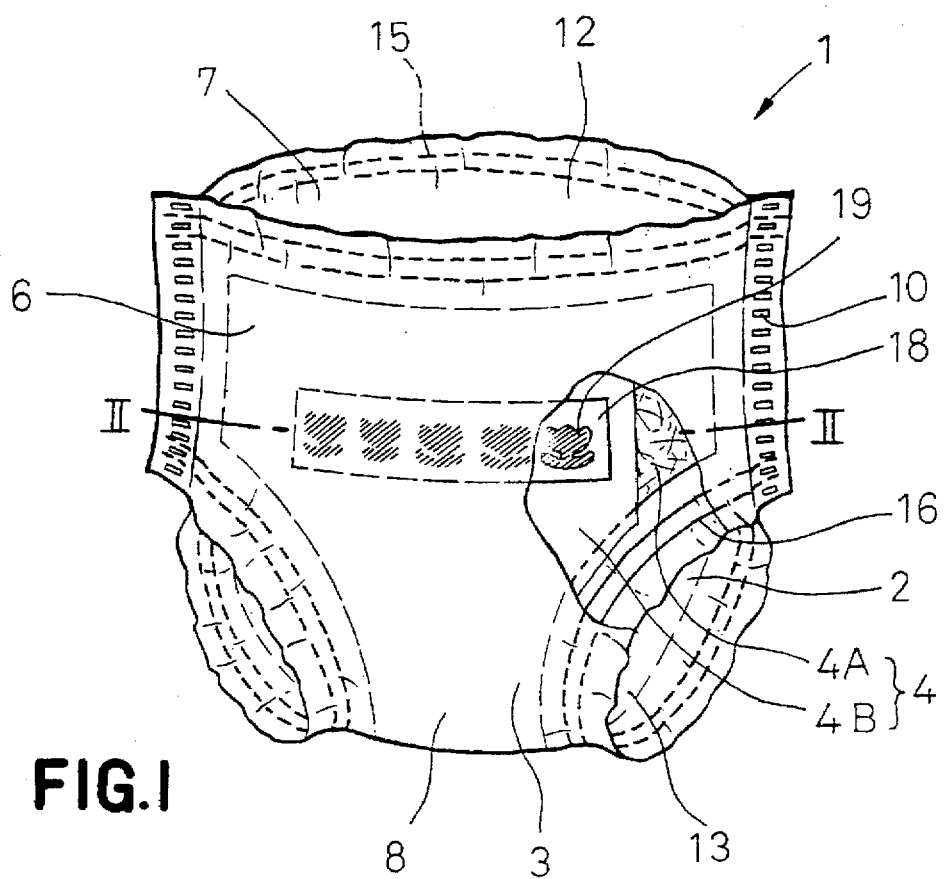
FIG. 1 is a perspective view showing an embodiment of the inventive diaper as partially broken away.

A diaper 1 of pants type shown by FIG. 1 in a perspective view as partially broken away comprises a liquid-permeable topsheet 2, a liquid-impermeable backsheet 3 and a liquid-absorbent core 4 disposed therebetween. The topsheet 2 and backsheet 3 are water-tightly bonded together over portions thereof extending outward beyond a peripheral edge of the core 4. The diaper 1 is composed of a front region 6, a rear region 7 and a crotch region 8 extending therebetween. The front and rear regions 6, 7 are placed one upon another along transversely opposite side edges thereof, respectively, with the topsheet 2 inside and integrally bonded together by bonding spots 10 arranged along the respective side edges intermittently in a vertical direction thereof so as to form a waist-opening 12 and a pair of leg-openings 13. The respective openings 12, 13 are provided along peripheral edges thereof with an elastic member 15 for the waist-opening 12 and elastic members 16 for the respective leg-openings 13. These elastic members 15, 16 are disposed between the topsheet 2 and backsheet 3 and bonded in a elastically stretched condition to an inner surface of at least one of these topsheet 2 and backsheet 3. The topsheet 2 may be made of nonwoven fabric or perforated plastic film and the backsheet 3 may be made of light-transmissive plastic film having a light-transmission rate of 20–80%, and more preferably of white or milk white air-permeable but liquid-impermeable film having a light-transmission rate of 30–70% and obtained by stretching plastic film containing inorganic particles, for example, of titanium oxide, barium sulfate or calcium carbonate. The core 4 comprises a core body 4A molded from fluff pulp and superabsorptive polymer particles into an hourglass-shape and a cover sheet 4B made of tissue paper adapted to cover the core body 4A. In the front region 6, there is disposed between the backsheet 3 and the core 4 an indicator 18 comprising a strip-like sheet extending parallel to the waist line which can indicate a mother that her baby has urinated. When this indicator 18 is wetted with urine, floral patterns 19 printed thereon become visible through the backsheet 3 whereby the mother can identify her baby's urination and know that the diaper 1 must be replaced by a fresh one as soon as possible.

Figure 2:
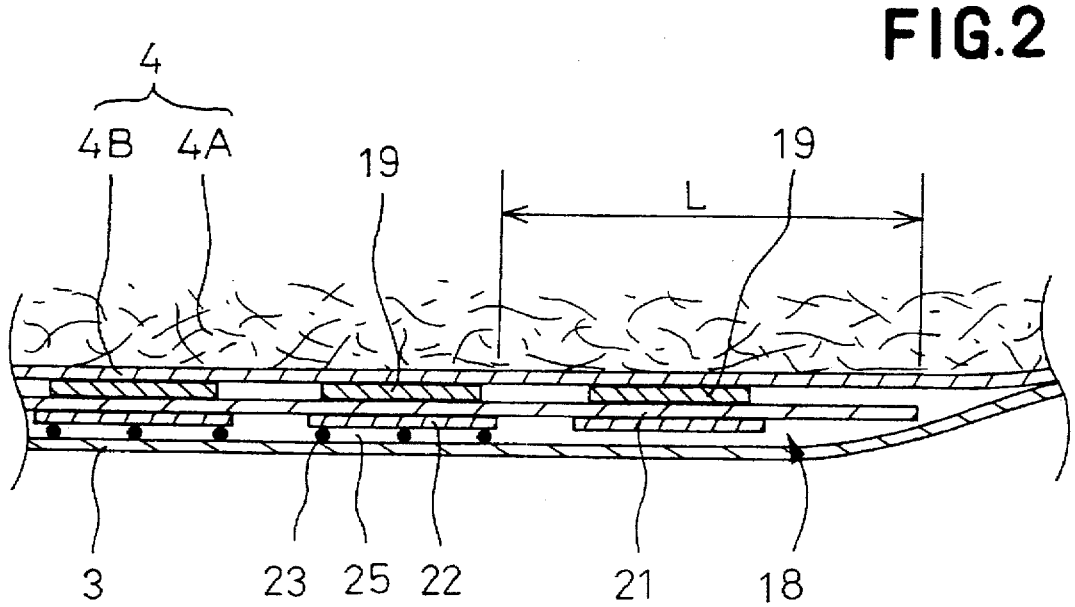
FIG. 2 is a sectional view taken along line II—II in FIG. 1.

FIG. 2 is a sectional view taken along line II—II in FIG. 1. As will be understood from FIG. 2, the indicator 18 comprises a hydrophilic base sheet 21, floral patterns 19 printed on an inner surface of the base sheet 21 and masking prints 22 arranged on the outer surfaces of the respective floral patterns 19 and covering at least these floral patterns 19 so that said floral patterns 19 are substantially invisible from the exterior so long as the diaper 1 is dry. The masking prints 22 corresponding to the respective floral patterns 19 are bonded by intermittently applied hot melt type adhesives 23 to the inner surface of the backsheet 3 so that at least regions of the base sheet 21 on which the floral patterns 19 are printed may be closely in contact with the backsheet 3. It should be understood, however, that a strip of the base sheet 21 sometimes may not be bonded to the backsheet 3 at transversely opposite sides of the strip defined by a length L. As shown, the floral patterns 19 are closely in contact with the core 4.

The base sheet 21 forming the indicator 18 may be made of printable hydrophilic paper having a basis weight of 15–40 g/m$^2$. The floral patterns 19 comprise a colored first coating layer deposited on one side of the base sheet 21 and is obtained by printing or applying aqueous ink or colorant including, for example, pigment having a color different from those of both the base sheet 21 and the masking prints 22 of 5–20% by weight, light scattering inorganic particles such as silica ($SiO_2$) or alumina ($Al_2O_3$) of 5–35% by weight, hydrophilic acryl binder of 5–25% by weight and water of 30–75% by weight. The floral patterns 19 appear white due to light scattering by the inorganic particles so long as they are dry but the light scattering is suppressed and develops its proper color as it is wetted with urine. Each masking print 22 comprises a second coating layer deposited on one side of the base sheet 21 so as to cover the floral patterns 19 and is obtained by printing or applying aqueous ink or colorant including, for example, inorganic particles such as those of silica or alumina of 10–40% by weight, hydrophilic acryl binder of 5–25% by weight and water of 40–85% by weight. The masking prints 22 appear white or milk white due to light scattering and prevent the floral patterns 19 from being visually recognized through the masking prints 22 so long as the prints 22 are dry. When they are wetted with urine, on the other hand, their light scattering is suppressed and their transparency is increased. The proper color of the floral patterns 19 which are different from the masking prints 22 as well as the base sheet 21 become apparent, allowing the floral patterns 19 to be visually recognized through the masking prints 22. The base sheet 21 cooperates with the masking prints 22 to cover up the floral patterns 19 when the base sheet 21 is dry and its cover-up effect is suppressed as the base sheet 21 is wetted with urine, allowing the floral patterns 19 to be easily recognized.

Although a color of the backsheet 3 is usually white or milk white, the color is not limited to such a color so far as it can cover-up the core 4. Should the indicator 18 placed on the inner side of the backsheet 3 be spaced from the backsheet 3, it would be difficult for the floral patterns 19 to be visually recognized through the backsheet 3 even when the indicator 18 is wetted with urine and the floral patterns 19 develop their vivid colors. According to the invention, such apprehension can be avoided by holding the indicator 18 closely in contact with the backsheet 3. Regions 25 (FIG. 2) are left between each pair of adjacent intermittently applied spots of adhesive 23 in which the indicator 18 and the backsheet 3 are not bonded together and the presence of urine in these regions 25 will further facilitate the floral patterns 19 to be visually recognized. There is an apprehension that the hot melt type adhesive 23 with which the indicator 18 is bonded to the backsheet 3 might permeate into the masking prints 22 and deteriorate the cover-up effect of the masking prints 22, since the masking prints 22 become transparent due to permeation of the hot melt type adhesive as if they are wetted with urine. To overcome such inconvenience, the adhesive 23 is intermittently applied to the indicator 18 at least in the regions corresponding to the floral patterns 19 and more preferably so as not to exceed 70% of each floral pattern's area. It is preferred to use the adhesive 23 containing no oily ingredients and not tending to permeate into the masking prints 22.

The indicator 18 bonded to the backsheet 3 has its longitudinally opposite margins each defined by a length L over which the indicator 18 is not bonded to the backsheet 3 and deformable so as to get a possibility that the indicator 18 may be brought into close contact with the core 4. Such an arrangement allows a quantity of urine to permeate from the core 4 through said margins into the regions of the floral patterns 19 bonded to the backsheet 3. The length L of each margin functioning as mentioned above is preferably 10 mm or longer. It is also possible, in order to make wetting of the indicator 18 further reliable, to bond the indicator 18 intermittently to the cover sheet 4B of the core 4 or to bond the backsheet 3 intermittently to said cover sheet 4B in the proximity of the indicator 18.

Figure 3:
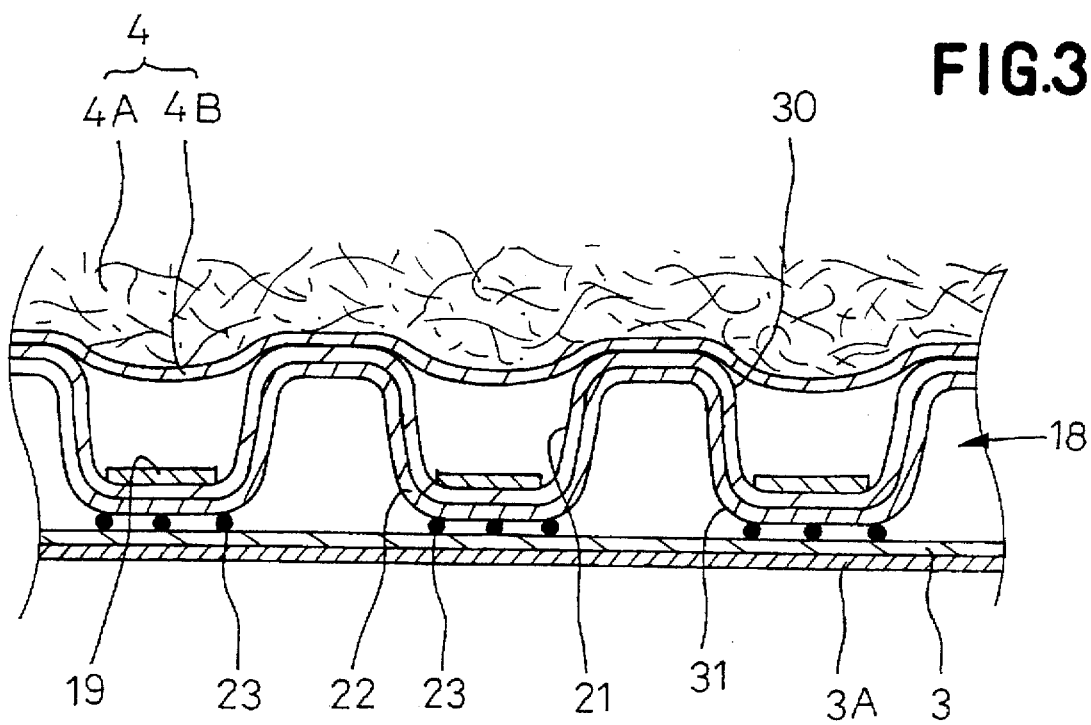
FIG. 3 is a view similar to FIG. 2 showing another embodiment of the inventive diaper.

FIG. 3 is a view similar to FIG. 2 showing another embodiment of the indicator 18. This indicator 18 longitudinally undulates and repeatedly presents crests 30 and bottoms 31. The indicator 18 is in contact with the core 4 at the crests 30 and bonded at the bottoms 31 to the backsheet 3 by means of adhesive 23. The floral patterns 19 are formed on the respective bottoms 31 and the masking print 22 is continuously formed all over the outer surface of the base sheet 21. A quantity of urine permeates from the core 4 through the crests 30 into the floral patterns 19. The indicator 18 of such an arrangement is advantageous in that the indicator 18 can be reliably in contact with the core 4 even when the backsheet 3 is spaced from the core 4 owing to the undulation.

Figure 4:
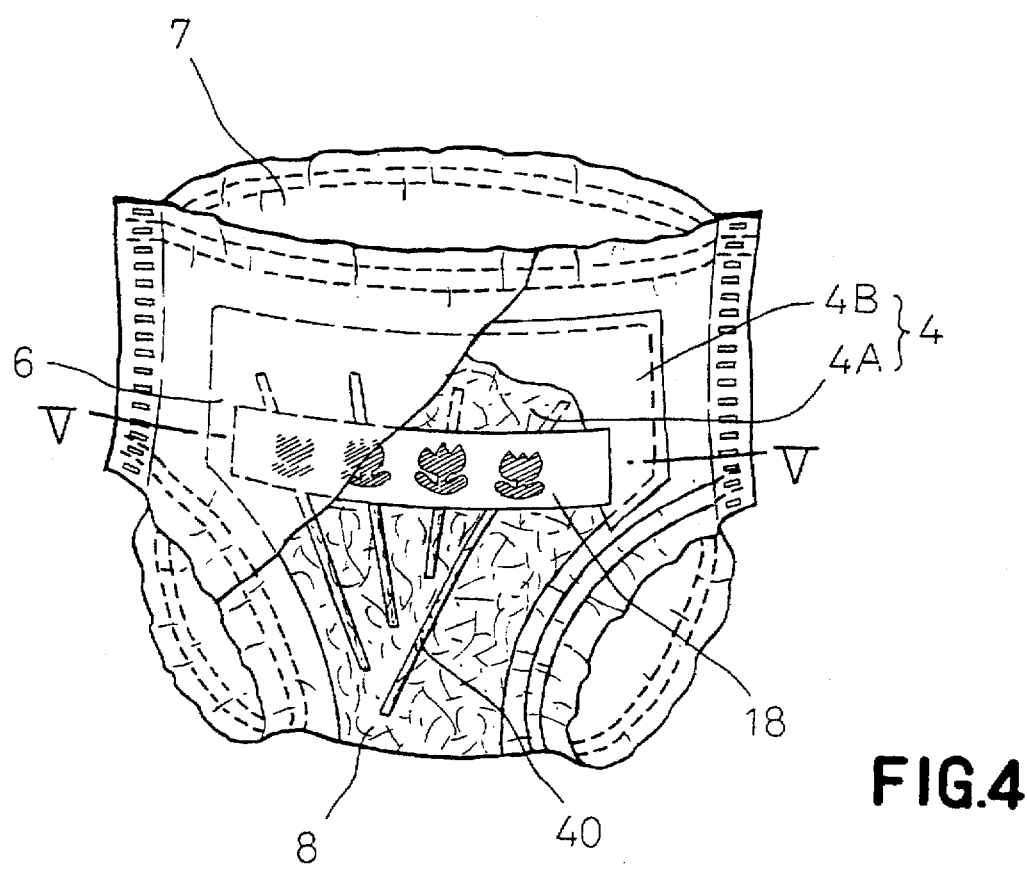
FIG. 4 is a view similar to FIG. 1 showing still another embodiment of the inventive diaper.
Figure 5:
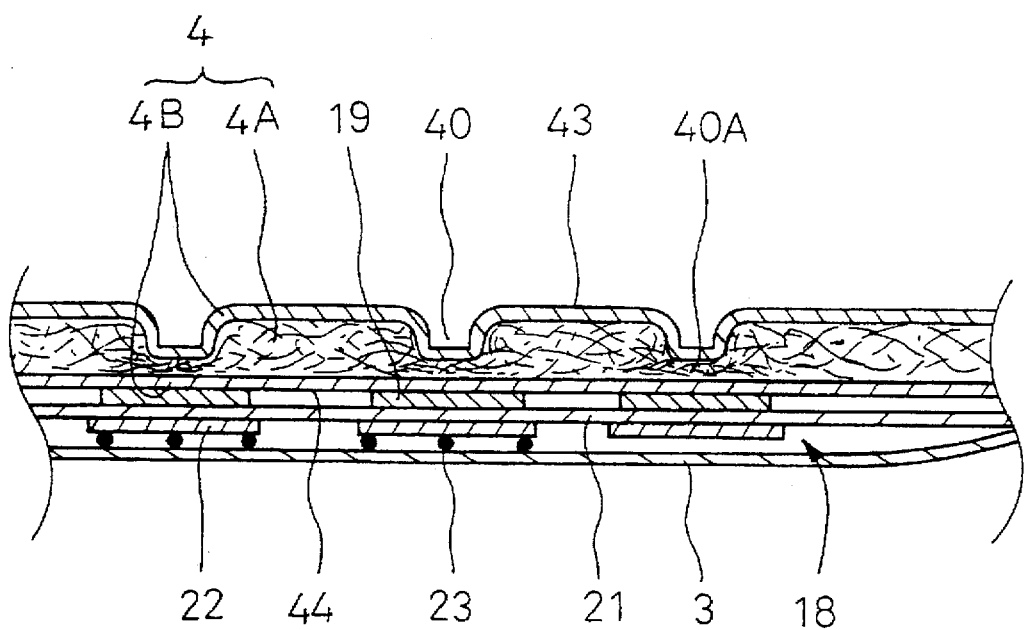
FIG. 5 is a sectional view taken along line V—V in FIG. 4.

FIGS. 4 and 5 are respectively a view similar to FIG. 1 showing still another embodiment of the diaper 1 and a sectional view taken along line V—V in FIG. 4. In this embodiment of the diaper 1, an inner surface of a core body 4A of the core 4 is formed with a plurality of grooves 40 extending from the front region 6 to the crotch region 8 and crossing the indicator 18 in the proximity of an outer surface 44 of the core body 4A. Inside the grooves 40, the fluff pulp of the core body 4A is locally compressed and presents a higher density at the bottoms 40A of the grooves 40 than the remainder regions so that a quantity of urine discharged onto the crotch region 8 rapidly spreads along the bottoms 40A of the grooves 40 and wets the indicator 18. With the core 4 comprising fluff pulp and superabsorptive polymer particles, diffusion of body fluids is generally slow, but the presence of the bottoms 40A of relatively high density facilitates the indicator 18 to be rapidly wetted with urine and thereby develops the proper color of the floral patterns 19 carried thereon even if the indicator 18 is located far from the crotch region 8.

To implement the invention, the indicator 18 is preferably made of hydrophilic material which is easily wetted with urine and, for example, the base sheet 21 is made of pulp fiber or rayon fiber. Colors of the base sheet 21, the floral patterns 19 and the masking prints 22 as well as the color of the backsheet 3 may be selected so that the proper color of the floral patterns 19 may develop as vivid as possible when the indicator 18 is wetted with urine. The masking prints 22 are not limited to the illustrated embodiments but they may be formed by applying ink or colorant on and adjacent the regions of the respective floral patterns 19. Also in such a case, the surface of the indicator 18 on which the masking prints 22 are formed is bonded to the backsheet 3. The base sheet 21 is not limited to the strip-like configuration as illustrated but may be implemented in other appropriate configurations. For example, if a rectangular base sheet 21 is employed, such a base sheet 21 may be provided with a surrounding margin having a width of 10 mm or larger along which the base sheet 21 is not bonded to the backsheet 3 in order to assure that the base sheet 21 be always in contact with the core 4. The floral patterns 19 may be replaced by any other appropriate patterns or by a coating layer deposited entirely over one surface of the base sheet 21. Materials used in the invention to form the coating layer may be colorant or ink, and a coating technique inclusive of a printing technique may be employed to form the coating layer. The materials used to form the coating layer may be added with ingredients such as polyacrylether to promote permeation of urine into the coating layer. If plastic film is used as the backsheet 3, nonwoven fabric may be applied on its outer surface to obtain a cloth-like touch.

With the disposable diaper provided by the invention, the indicator comprises the first coating layer adapted to develop a vivid color as it is wetted and the hydrophilic base sheet on which the first coating layer formed in an appropriate pattern wherein the indicator is intermittently bonded to the inner surface of the backsheet so that a quantity of urine may permeate and spread from the liquid-absorbent core through the base sheet into the first coating layer so as to reliably wet this layer and consequently the first coating layer may develop its proper color. The indicator bonded to the backsheet has its longitudinally opposite margins and/or peripheral edge not bonded to the backsheet so as to be deformable or is undulated and thereby its contact with the liquid-absorbent core is assured. In one embodiment of the diaper in which a plurality of grooves having their bottoms of relatively high density formed by locally compressing the liquid-absorbent core including pulp fiber extend between one of the front and rear regions and the crotch region and crossing the indicator, the indicator is wetted with urine and develops a proper color upon urination even if the indicator is located far from the crotch region. According to the invention, use of such an indicator does not adversely affect a productivity of the diaper since the indicator can be manufactured by a process independent of main manufacturing processes for the diaper.

What is claimed is:

1. A disposable diaper comprising a liquid-permeable topsheet, a liquid-impermeable backsheet, a liquid-absorbent core disposed therebetween, and indicator means provided on a front or rear region of the diaper so as to be revealed as the indicator means is wetted with urine and thereby to allow occurrence of body fluid excretion to be visually recognized externally of the diaper, the disposable diaper being characterized by that:

a. the backsheet is light-transmissive;

b. the indicator means comprises a hydrophilic base sheet, a first coating layer formed on one side of the base sheet and having a color different from that of the base sheet, and a second coating layer formed on the other side of the base sheet or an upper surface of the first coating layer so as to substantially cover up the color of the first coating layer when the indicator means is dry but to become transparent and thereby to reveal the color as the indicator means is wetted with urine;

c. the first coating layer comprises at least one of silica and alumina particles, and water-absorptive binder and colorant;

d. the second coating layer comprises at least one of silica and alumina particles, and hydrophilic binder; and e. the indicator means is attached to the diaper by intermittently bonding said second coating layer to inner surface of said backsheet.

2. The diaper according to claim 1, wherein the backsheet is made of plastic film having a light-transmission rate of 20–80%.

3. The diaper according to claim 1, wherein the indicator means is bonded to said backsheet by intermittent spots of hot melt type adhesive.

4. The diaper according to claim 3, wherein the hot melt type adhesive contains no oily ingredients.

5. The diaper according to claim 1, wherein the indicator means has the first coating layers intermittently arranged on the base sheet.

6. The diaper according to claim 1, wherein the indicator means has the first coating layers and second coating layers both intermittently arranged on the base sheet.

7. The diaper according to claim 1, wherein the base sheet for the indicator means includes a peripheral region having a width of 10 mm or larger left not bonded to the backsheet.

8. The diaper according to claim 1, wherein the base sheet is a narrow strip of sheet having its longitudinally opposite margins each extending by 10 mm or longer left not bonded to the backsheet.

9. The diaper according to claim 1, wherein the base sheet presents undulation in one direction and is bonded respectively at bottoms of the undulation to the backsheet, on one hand, and spaced respectively at crests of the undulation from said backsheet but able to contact the core at said crests; and wherein the first coating layer is formed at least on said bottoms of the undulation.

10. The diaper according to claim 1, wherein the core contains fluff pulp; wherein a plurality of grooves formed by locally compressing the pulp and having their bottoms of relatively high density extend between one of the front and rear regions and the crotch region; and wherein the grooves cross the indicator means provided on the one of the front and rear regions.

* * * * *